United States Patent [19]

Orth et al.

[11] Patent Number: 4,942,239

[45] Date of Patent: Jul. 17, 1990

[54] PROCESS FOR THE PRODUCTION OF 2-HYDROXYPYRIDINE

[75] Inventors: Winfried Orth, Hassloch; Michael Hassler, Bruchsal; Hans W. Kleffner, Battenberg; Wolfgang Weiss, Neckarhausen, all of Fed. Rep. of Germany

[73] Assignee: Rutgerswerke AG, Fed. Rep. of Germany

[21] Appl. No.: 317,537

[22] Filed: Mar. 1, 1989

[30] Foreign Application Priority Data

Apr. 28, 1988 [DE] Fed. Rep. of Germany ....... 3814358

[51] Int. Cl.$^5$ ............................................ C07D 213/64
[52] U.S. Cl. ..................................... 546/290; 546/303
[58] Field of Search ................................ 546/290, 303

[56] References Cited

U.S. PATENT DOCUMENTS 3,355,456  11/1967  Sexton .................................. 546/303

OTHER PUBLICATIONS

Klingsberg, "Pyridine and Its Derivatives", Part Two, Interscience Publishers, p. 349 (1961).

*Primary Examiner*—Alan L. Rotman
*Attorney, Agent, or Firm*—Bierman and Muserlian

[57] ABSTRACT

A process for the production of 2-hydroxypyridine from 2-chloro-pyridine which is reacted with an aqueous alkaline solution in the presence of a tertiary alcohol.

5 Claims, No Drawings

PROCESS FOR THE PRODUCTION OF 2-HYDROXYPYRIDINE

FIELD OF THE INVENTION The invention relates to a new process for the production of 2-hydroxypyridine or 2-(1H)-pyridinone which serves as an important intermediate product in the production of pharmaceuticals such as penicillin and cephalosporin derivatives.

THE PRIOR ART

In prior art methods, such as U.S. Pat. No. 1,778,784, 2-hydroxypyridine was produced by the hydrolysis of 2-chloro-pyridine in concentrated hydrochloric acid at 150° C under pressure. Despite these extreme reaction conditions and a reaction time of several hours, a yield of only 24 percent was obtainable. According to J. Chem. Soc., B (1968), 492, an improvement in the above process could be obtained by reacting 2-chloro-pyridine with potassium ethylate and subjecting the formed 2-methoxypyridine to hydrolysis in an aqueous acid solution. While an increase in yield of up to 70 percent could be achieved thereby, the reaction required a two-stage process.

SUMMARY OF THE INVENTION

The objection of the invention is to simplify the above-described reaction and increase the yield of 2-hydroxypyridine. In the inventive process, 2-chloropyridine is reacted with an aqueous alkaline solution in the presence of a tertiary alcohol.

DETAILED DESCRIPTION OF THE INVENTION

It has been surprisingly found that high purity 2-hydroxypyridine can be produced from 2-chloro-pyridine in a one-stage reaction with a superior yield, if 2-chloro-pyridine is reacted with an aqueous alkaline solution in the presence of a tertiary alcohol. This is surprising inasmuch as in the absence of the tertiary alcohol, no reaction between 2-chloro-pyridine and the concentrated potassium hydroxide occurs at reflux.

As the tertiary alcohol, all tertiary alcohols can be used provided they are liquid under the reaction conditions (80°–120° C). Particularly suitable in the process are tertiary butyl alcohol and amyl alcohol. The tertiary alcohol is employed in a quantity of 0.5 to 5 times the quantity of the aqueous alkaline solution.

Aqueous alkaline solutions are defined as aqueous solutions of alkali metal hydroxides, ammonia, primary, secondary or tertiary alkylamines, or alkaline earth metal hydroxides. The reaction improves in direct correlation with the alkalinity of the solution and therefore, concentrated alkali metal hydroxides, in particular, potassium hydroxide, are preferred.

The quantity of alkaline substance must be such that after separation of the chlorine and neutralization to chloride, a distinct alkaline reaction in the reaction medium continues to exist. Preferably, the alkaline substance is present in a quantity 1.5 to 3 times the equimolar quantity of the 2-chloro-pyridine.

The inventive reaction occurs best at elevated temperatures, preferably at temperatures in the boiling range of the reaction mixture. The reaction mixture is heated, preferably with reflux, at atmospheric pressure. The reaction can also be conducted at an elevated pressure and higher temperatures.

After the reaction has been concluded, the reaction mixture is processed in a manner heretofore known. The tertiary alcohol is recovered, the excess alkaline substance is neutralized, and the formed salts are separated from the desired 2-hydroxypyridine.

The present invention is hereinafter described in greater detail with reference to examples, which are not to be construed as limiting the scope thereof.

EXAMPLE

A mixture of 600 ml of tertiary amyl alcohol and 330 g (about 5.3 moles) of potassium hydroxide (about 90 percent) is heated at reflux (at about 118° C) and then, 227 g of 2-chloro-pyridine (2 moles) were added dropwise within 1.5 hours (the sump temperature fell from 118° C to 105° C) and reflux was continued for 24 hours.

After boiling, the t-amyl alcohol was distilled off. 1000 ml of water were added and the mixture was again distilled to the extent that the residue was still able to be stirred in the cold state (about 600 ml were distilled off). The mixture was then cooled. During cooling, the pH was adjusted to between 5 and 6 with about 340 ml cf concentrated HCl and the remaining water was distilled off. The residue was again cooled to 60° C and 700 ml of methanol were slowly mixed therewith. The mixture was further cooled to room temperature and the precipitated inorganic salts were filtered off. The remaining product was rinsed with about 100 ml of methanol. The combined methanol phases were concentrated and the residue was distilled under vacuum and the product passing over at 174° to 178° C/14 mm was collected to obtain 176.5 g (92 % of theoretical yield) of 99.7% 2-hydroxypyridine.

While the invention has been described in detail and with reference to specific embodiments thereof, it will be apparent to one skilled in the art that various changes and modifications can be made therein without departing from the spirit and scope thereof.

What is claimed is:

1. A process for the production of 2-hydroxypyridine comprising reacting 2-chloro-pyridine with an aqueous concentrated potassium hydroxide solution in the presence of a tertiary alcohol at reflux at atmospheric pressure.

2. The process of claim 1 wherein said tertiary alcohol is tertiary butyl alcohol.

3. The process of claim 1 wherein said tertiary alcohol is tertiary amyl alcohol.

4. The process of claim 1 wherein the potassium hydroxide is present in a quantity of 1.5 to 3 times the equimolar quantity of said 2-chloro-pyridine.

5. The process of claim 1 wherein said tertiary alcohol is present in a quantity of 0.5 to 5 times that of said aqueous alkaline solution.

* * * * *